United States Patent [19]
Nelson

[11] Patent Number: 4,501,970
[45] Date of Patent: Feb. 26, 1985

[54] FLUOROMETER

[75] Inventor: Keith E. Nelson, Virdes, Calif.

[73] Assignee: Dynatech Laboratories Incorporated, Alexandria, Va.

[21] Appl. No.: 433,825

[22] Filed: Oct. 12, 1982

[51] Int. Cl.³ ............................................. G01N 21/64
[52] U.S. Cl. ................................ 250/458.1; 250/461.1; 356/318
[58] Field of Search .................. 250/328, 458.1, 459.1, 250/461.1, 461.2; 356/317, 318, 244, 417

[56]  References Cited
U.S. PATENT DOCUMENTS

| | | | |
|---|---|---|---|
| 3,763,374 | 10/1973 | Tiffany et al. | 250/363 |
| 3,811,777 | 5/1974 | Chance | 250/458.1 |
| 3,883,247 | 5/1975 | Adams | 250/461.2 |
| 3,899,213 | 8/1975 | Fantasia et al. | 250/461.1 |
| 3,950,649 | 4/1976 | Yonekubo | 250/458.1 |
| 4,004,150 | 1/1977 | Natelson | 250/328 |
| 4,278,887 | 7/1981 | Lipshutz et al. | 250/432 |

FOREIGN PATENT DOCUMENTS 149574 7/1981 Fed. Rep. of Germany .

OTHER PUBLICATIONS

Huke et al., "Measurement of Fluorescent Spectra of Liquids with a Modified Beckman DU Spectrophotometer," *Jour. of Optical Soc. of Amer.*, vol. 43, No. 5, May 1953, p. 400+.
Danilin et al., "Low-Temperature Spectrofluorometer Attachment," Ind. Lab. (U.S.A.), vol. 45, No. 9, Mar. 1980.

*Primary Examiner*—Janice A. Howell
*Attorney, Agent, or Firm*—LeBlanc, Nolan, Shur & Nies

[57]  ABSTRACT

A sensitive frontal approach fluorometer which is suitable for measuring the fluorescence of samples in open top microtest wells and which has an optical system for (a) directing an exciting light downwardly into the well's open top to fluorescently excite the sample and (b) detecting the sample's emitted light which passes upwardly through the well's open top.

8 Claims, 4 Drawing Figures

FLUOROMETER

FIELD OF INVENTION

This invention relates to fluorometers and is particularly concerned with a novel optical system for a fluorometer of the frontal approach type. The fluorometer of this invention is particularly suitable for measuring the fluorescence of substances in microtest wells (or microtiter wells, as they are also called) and other similar vessels.

For purposes of this specification, a fluorometer of the frontal approach type is one in which the exciting light or radiation enters through the open top of a sample-holding vessel and in which the detected emitted light (resulting from fluorescent excitation of the material) exits through the vessel's open top.

The term "light" as used in this specification refers to both non-visible light (e.g., ultraviolet light) and visible light, that is, light visible to the naked eye.

BACKGROUND

Prior to this invention various fluorometers have been used in a wide variety of applications for measuring the fluorescence of fluorescently excitable materials. For example, fluorometers are used in junction with fluorescent assays to detect and measure the quantities of immunological and non-immunological substances.

In carrying out fluorescent assays, microtest plates (or microtitration plates, as they are also called) and strips of microtest wells are often used. Microtest plates are formed with a multiplicity of wells which are joined together in a molded one-piece structure for containing microliter quantities of fluid samples in liquid or solid form. Examples of a microtest plate and microtest wells in strip form are described in U.S. Pat. No. 4,154,795 which issued to A. C. Thorne on May 15, 1979.

The use of microtest plates and microtest strips of wells in fluorescent and other types of assays offers several important advantages. First, they permit the mass preparation of a large number of test sample solutions at the same time. Second, they are more convenient to handle as compared with individual test tubes. Third, they can easily and inexpensively be washed. Fourth, they are inexpensive and disposable. Fifth, they are customarily formed from plastic materials which are not fragile like glass. Sixth, they can be made from a material having an ability to attract certain molecules such as protein molecules so that they can serve as a solid phase in an immunoassay.

Some fluorometers are not sufficiently sensitive to measure the fluorescence of the small, microliter quantities of the relatively low fluorescent samples which are prepared with the microtest plate and strip equipment described above. Other fluorometers, while having sufficient sensititvity, are usually unsuitable for measuring the fluorescence of substances in microtest wells because they are designed to direct the exciting light and/or the sample's emitted light through a wall of the sample-holding vessel. As a result, the microtest plates and strips, which are customarily molded from plastic materials having a substantial level of native fluorescence, are excessively excited to produce spurious light emissions which interfere with and impair accurate measurements of the intensity of the light emitted by the fluorescently excited test sample itself.

SUMMARY AND OBJECTS OF INVENTION

With the foregoing in mind, the general aim and purpose of this invention is to provide a novel fluorometer which meets both of the foregoing requirements, namely high sensitivity and suitability for measuring the fluorescence of microliter quantities of test samples in microtest plate wells and similar vessels.

A more specific object of this invention is to provide a frontal approach fluorometer with a novel optical system which utilizes a special focusing technique to provide for a highly efficient transfer of radiation energy from an excitation light source to the sample and also to provide for a highly efficient transfer of emitted light from the fluorescently excited sample to a detector.

In accordance with this invention, the optical system comprises a pair of bi-convex lenses or double-convex lenses, as they are also called, one for transmitting the exciting light to the test sample, the other for transmitting the light emitted by the fluorescently excited material to a photodetector.

On the exciting light side of the optical system, the distance of the light path followed by the exciting light between the exciting light source and the sample in the microtest well or other sample-holding vessel is set to equal a multitude (e.g., four times) the focal length of the lens used for transmitting the exciting light, and the lens for the exciting light is located at the midpoint of the exciting light's path. The light path distance between the exiting light source and the lens for the exciting light is therefore equal to twice the lens' focal length. Likewise, the light path distance between the exciting light's lens and the sample in the well is also equal to twice the lens' focal length. The image of the light source will therefore be focused sharply on the sample in the well to maximize the fluorescent excitation of the sample for a given intensity of the exciting light. A corresponding focusing technique is applied to the lens for the sample's emitted light.

Thus, on the emitted light side of the optical system, the total length of the light path between the sample in the well and the fluorometer's photodetector is set to equal a multiple (e.g., four times) the focal length of the lens used for transmitting the sample's emitted light, and the lens for the emitted light is located at the midpoint of the light path followed by the emitted light. The light path distance between the lens for the emitted light and the sample in the well is therefore equal to twice the lens' focal length, while the light path distance between the lens for emitted light and the photodetector is also equal to twice the lens' focal length so that the full image of the sample is sharply focused on the photodetector to maximize the intensity of the light detected by the photo- detector.

Because of the foregoing focusing conditions, the sensitivity of the optical system is significantly enhanced as compared with systems using unfocused light.

According to another feature of this invention the total length of the light path for the exciting light and the total length of the light path for the emitted light are selectively and independently adjustable to compensate for imperfections in the lenses which cause the lenses' focal lengths to deviate from a design or ideal value. The length of the light path for the exciting light may be adjusted by adjusting the position of the object, namely the light source or an optical stop lying in front of the light source. On the emitted light side of the optical system, the light path for the emitted light is adjusted by adjusting the position of the photodetector.

In addition to the foregoing, the optical system of this invention includes a novel mirror and mask arrangement which lies between the two lenses. This mirror and mask arrangement performs a number of important functions. First, it downwardly reflects the exciting light to cause it to enter the sample-holding well through the open top thereof. Second, it works in conjunction with the lens for the exciting light to direct the exciting light beam through the well's open top without striking the well's side wall or the surface regions around the open top of the well. Third, it reflects the sample's emitted light, which passes upwardly through the well's open top, to cause it to pass through the lens for the emitted light. Fourth, it keeps the sample's emitted light from entering the exciting light channel lying between the mirror arrangement and the exciting light source, and it also keeps the exciting light from entering the emitted light channel lying between the mirror arrangement and the photodetector. Finally, it reduces the amount of scattered radiation in the emitted light channel to reduce the noise signal level in the fluorometer's photodetector.

Further objects of this invention will appear as the description proceeds in connection with the below-described drawings and the appended claims.

DETAILED DESCRIPTION

Figure 1:
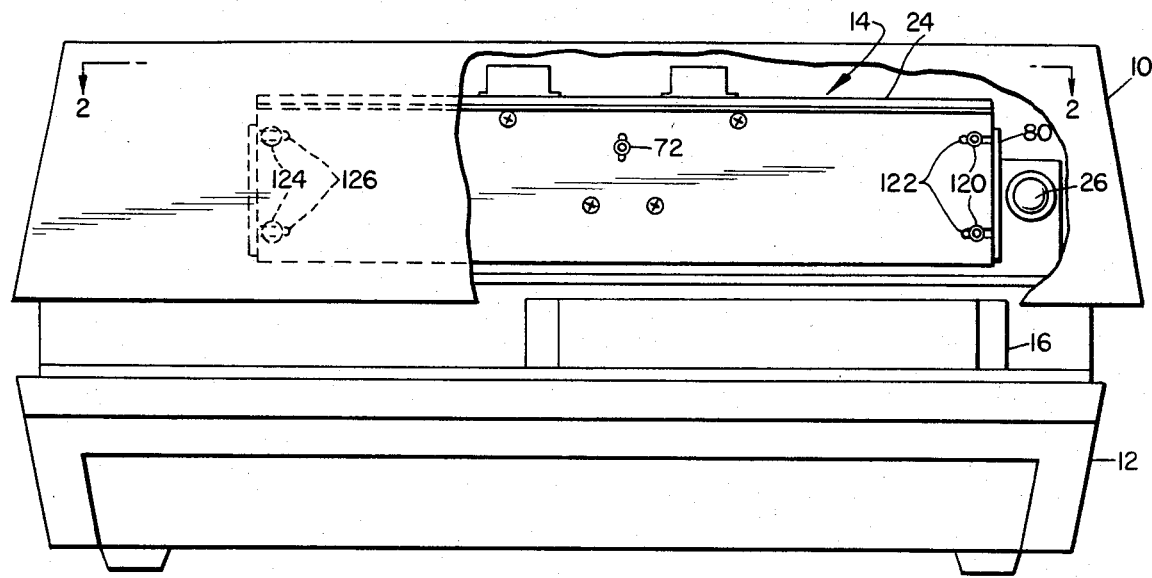
FIG. 1 is a front elevation of a fluorometer incorporating the principles of this invention and showing the outer cabinet partially broken away to illustrate the optical system's inner housing.
Figure 2:
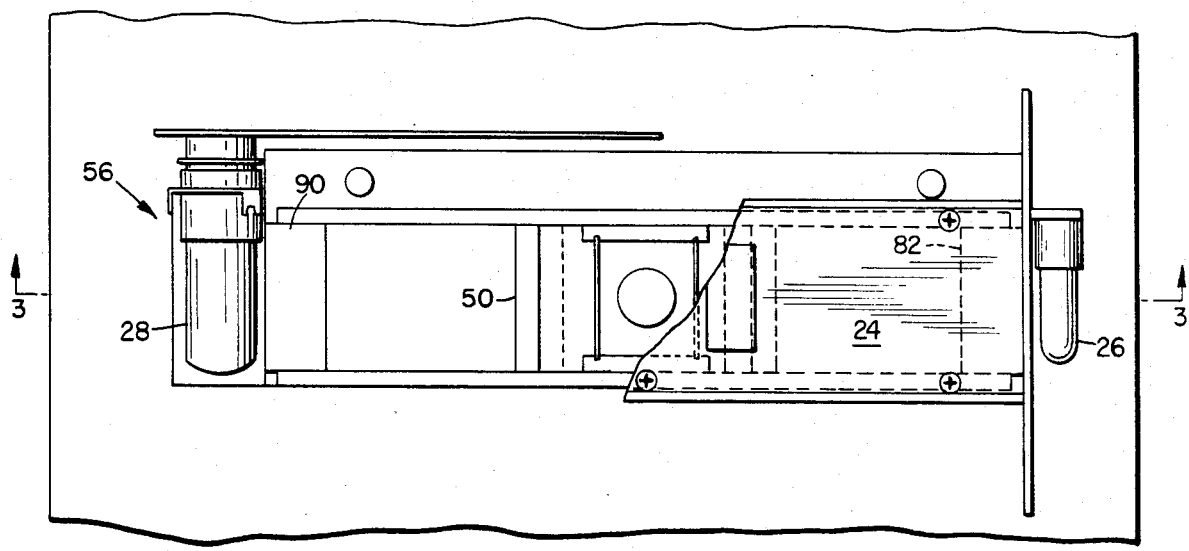
FIG. 2 is a top plan view of the fluorometer shown in FIG. 1, with the top cabinet wall broken away to illustrate the optical system's housing.

Referring to the drawings and particularly to FIGS. 1 and 2, the fluorometer incorporating the principles of this invention comprises an outer cabinet 10, a support base 12, an optical system 14, and a movable carriage 16 for supporting a microtest plate 18. Cabinet 10 is preferably light tight. Base 12 supports carriage 16.

Microtest plate 18 contains a multiplicity of open form. Plate 20 may be of the type shown in the previously top wells 20 for receiving and holding test samples in liquid mentioned U.S. Pat. No. 4,154,795 or it may be of the type shown in U.S. Pat. No. 3,356,462 which issued to N. M. Cooke et al on Dec. 5, 1967. The disclosures of these patents are incorporated into this specification by reference.

Wells 20 are uniformly spaced apart in twelve parallel spaced apart rows of wells with eight wells in each row to provide the standard total of 96 wells. Each of the wells 20 is formed with a cylindrical side wall and a suitable bottom wall. Wells 20 depend from a top wall 22 of the plate.

The carriage 16 together with plate 18 and optical system 14 are all mounted in cabinet 10. Carriage 16 lies below the optical system 14 as shown.

Figure 3:
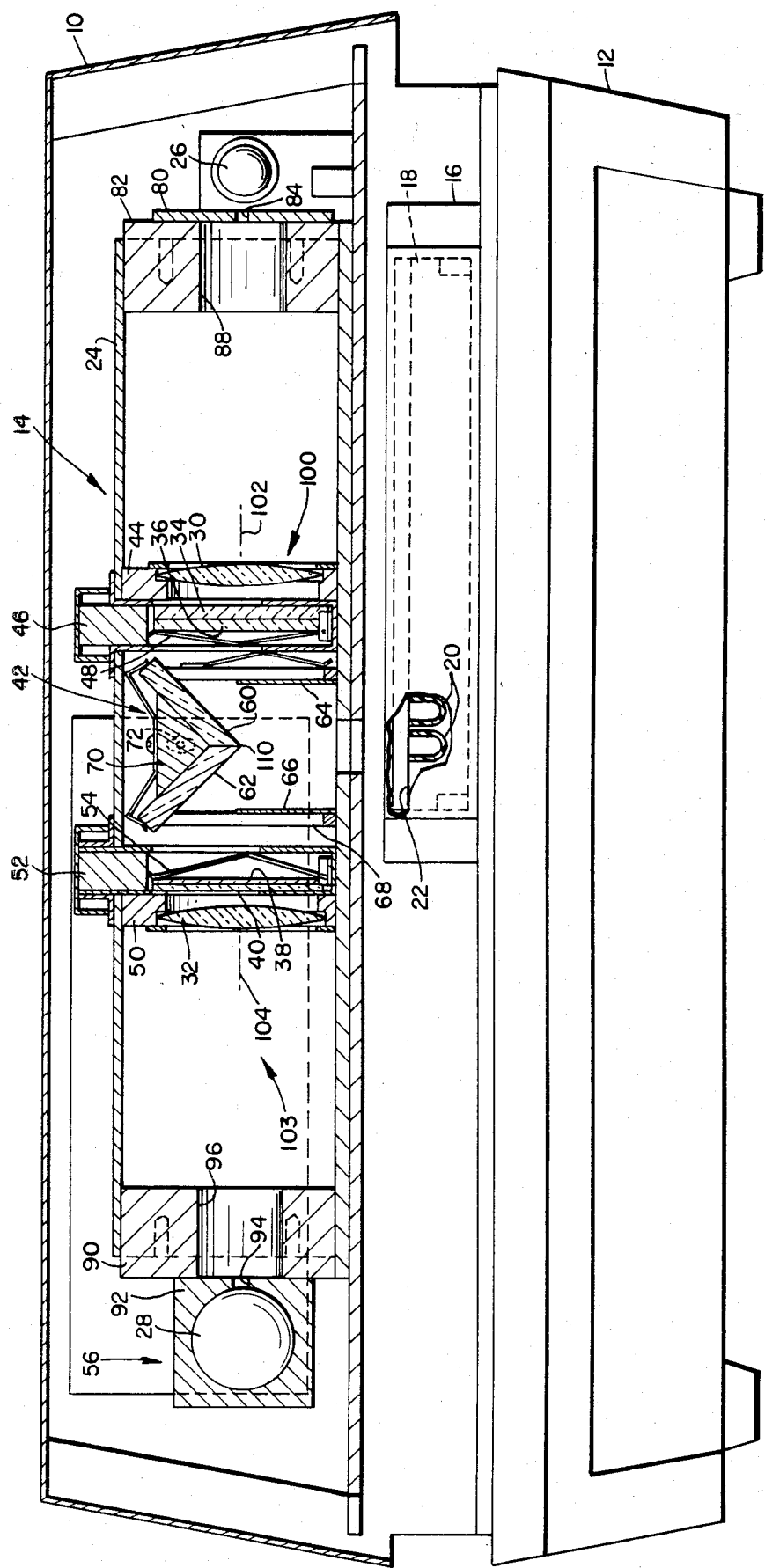
FIG. 3 is a section taken substantially along lines 3—3 of FIG. 2.
Figure 4:
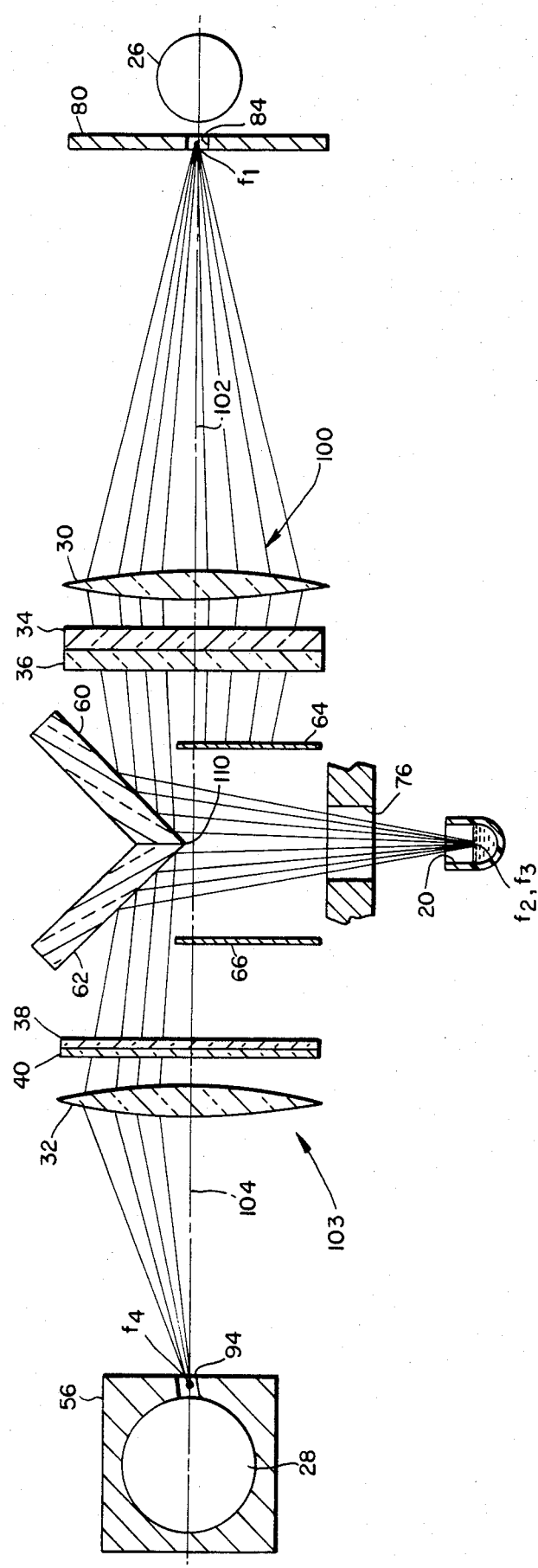
FIG. 4 is an elevation of the illustrated optical system in partially schematic form.

Referring now to FIGS. 3 and 4, optical system 14 comprises an elongated housing 24 of rectangular cross-section, a suitable source of exciting light or radiation such as an ultraviolet lamp 26, a suitable photodetector such as a photomultiplier 28, a pair of bi-convex lenses 30 and 32, a first pair of filters 34 and 36, a second pair of filters 38 and 40, and a mirror and optical mask assembly 42.

As shown in FIG. 3, lens 30 is mounted in a suitable holder 44. Filters 34 and 36 are mounted side by side in another suitable holder 46 and are releasably retained in place by a leaf spring 48.

Lens 32 is also mounted in a suitable holder 50. Filters 38 and 40 are mounted side by side in another suitable holder 52 and are retained in place by a leaf spring 54.

Holders 44, 46, 50 and 52 are all mounted in housing 24 as shown. Holder 46 and filters 34 and 36 are removable as a unit through an opening in the top of housing 24. Similarly, holder 52 and filters 38 and 40 are also removable as a unit through another opening in the top wall of housing 24.

Still referring to FIG. 3, lamp 26 is mounted exteriorly of housing 24 at one end thereof, and photomultiplier 28 is mounted in a holder 56 at the opposite end of housing 24. The mirror and mask assembly 42 is mounted in housing 24 centrally between the housing's opposite ends. As shown, mirror and mask assembly 42 comprises a pair of light-reflecting mirrors 60 and 62 and a pair of optical masks 64 and 66. Masks 64 and 66 are rigidly mounted on a support frame 68 which in turn is mounted in housing 24. Mirrors 60 and 62 are mounted on a support member 70 which in connection 72, which permits selective vertical adjustment of the turn is mounted on frame 68 by means of a screw and slot assembly of mirrors 60 and 62 and support member 70.

The assembly of mirrors 60 and 62 defines a V-shaped configuration in which one of the mirrors forms one leg of the V-shaped configuration and the other mirror forms the other leg of the V-shaped configuration. Mirrors 60 and 62 abut against each other at the apex of the V-shaped configuration. The angle included between mirrors 60 and 62 is preferably 90°. Mirrors 60 and 62 are symmetrical about a vertical plane passing through the interface between the apex-defining, abutting edges of the mirrors. The apex defined by the abutting ends of the mirrors 60 and 62 is indicated at 110 and lies vertically above an aperture 76 which is formed through the bottom wall of housing 24 above plate 18 in carriage 16. The wall region defining aperture 76 constitutes an optical stop.

Still referring to FIG. 3, a further optical stop 80 is mounted on the outer end of a support block 82 which is slidably received in the end of housing 24 adjacent to lamp 26. The optical stop 80 is formed with a central opening 84 lying along an axis which normally intersects the longitudinal axis of lamp 26. Aperture 84 is axially aligned with and opens into an enlarged aperture 88 which is formed through support block 82. Optical stop 80 lies on the outer side of housing 24 between lamp 26 and support block 82. Aperture 84 lies closely adjacent to lamp 26 as shown. The diameter of the support block's aperture 88 is substantially larger than that of aperture 82 to allow the rays of the exciting light passing through aperture 84 from lamp 26 to diverge in the manner shown in FIG. 4.

Still referring to FIG. 3, the photomultiplier holder 56 is mounted on the outer end of another support block 90 which is slidably received in the end of housing 24 opposite from support block 82. The wall region of holder 56 abutting support block 90 defines another optical stop 92 having a central light-transmitting aperture 94. The inner end of aperture 94 axially aligns with an enlarged aperture 96 which is formed through support block 90. Aperture 96 is sufficiently large in diameter to allow converging light rays from lens 32 to enter aperture 94 without being blocked. Aperture 94 to photomultiplier 28.

Holder 56 is sufficiently large to cover the aperture 96 in support block 90. Similarly, optical stop 80 is sufficiently large to cover the aperture 88 in block 82 except for the opening provided by aperture 84. Housing 24 is preferably light tight except for apertures 84 and 76.

As shown in FIGS. 3 and 4, lens 30 and filters 34 and 36 are arranged between optical stop 80 and mirror 60 to form an exciting light channel 100 for system 14. The principal axis or centerline of lens 30 is indicated at 102 in FIGS. 3 and 4 and axially aligns with apertures 84 and 88. Lens 30 is positioned between optical stop 80 and filter 34. Lens 30 lies closely adjacent to filter 34 so that the spacing between lens 30 and filter 34 is considerably smaller than the spacing between lens 30 and optical stop 80. Filter 36 is positioned between filter 34 and mirror 60 and is spaced from mirror 60 as shown. Filter 36 may abut against filter 34 as shown.

Still referring to FIGS. 3 and 4, lens 32 and filters 38 and 40 are arranged between mirror 62 and optical stop 92 to form an emitted light channel 103 for system 14. The principal axis or centerline of lens 32 is indicated at 104 and axially aligns with the axes of apertures 94 and 96. In the illustrated embodiment, the principal axis 104 of lens 32 also axially aligns with the principal axis 102 of lens 30.

Lens 32 is positioned between filter 40 and aperture 94 and lies closely adjacent to filter 40 so that the distance between lens 32 and filter 40 is considerably smaller than the distance between lens 32 and aperture 94.

As shown in FIG. 4, light emitted by lamp 26 passes through the optical stop's aperture 84. From there, the rays of the exciting light diverge to lens 30. These light rays are refracted by lens 30 so that the light rays passing beyond 34 and 36. In this embodiment, filters 34 and 36 pass just ultraviolet light, while rejecting all other wave lengths.

The apex 110 of mirror assembly 60, 62 lies on the aligned principal axes 102 and 104 of lenses 30 and 32. Mirrors 60 and 62 and masks 64 and 66 are symmetrically arranged about a vertical plane passing through the mirrors' apex 110 and containing the longitudinal axis of aperture 76. Mask 64 is located vertically below the reflecting surface of mirror 60 and has its upper edge lying just above the aligned principal axes of the lenses so that it lies just above the level of the apex 110. Accordingly, light passing through the lower half of lens 30 below the principal axis 102 will be blocked by mask 64, thus preventing the exciting light from passing into the system's emitted light channel 103.

Because of the foregoing arrangement of mirror 60 and mask 64, only the light passing through the upper half of lens 30 will strike and be reflected by mirror 60. The converging column of light striking mirror 60 will be reflected downwardly at a small acute angle to a vertical plane because of the 45° angle which the reflecting surface of mirror 60 makes with the principal axis of lens 30.

The column of excited light reflected by mirror 60 passes downwardly through aperture 76 and through the open top of one of the sample-holding wells 20 which is selectively positioned to lie vertically below aperture 76 in alignment with the longitudinal axis of aperture 76. The column of exciting light entering well 20 strikes the test sample in the well. As a result, the fluorescently excitable substance or substances in the test sample will be fluorescently excited to emit light which passes upwardly through the open top of well 20 and through aperture 76 to strike the reflecting surface of mirror 62. The reflecting surface of mirror 62 intersects the lenses' principal axes 102, 104 at a 45° angle.

Because of the angulation of the reflecting surface of mirror 62, the rays of the sample's emitted light striking mirror 62 will be reflected towards lens 32 and will diverge in the direction of lens 32 as shown in FIG. 4. The diverging rays of light reflected from mirror 62 pass through filters 38 and 40 before arriving at lens 32.

In the illustrated embodiment, filter 38 is designed to reject light in the ultraviolet range while passing all other wave lengths above the ultraviolet range. Filter 40 is of the band pass type for passing just one preselected wave length (or a narrow wave length band) of the emitted light passed by filter 38. The light wave length passed by filter 40 is selected to measure the fluorescence of light emitted by a particular substance of interest in the sample in well 20.

Mask 66 is positioned vertically below the reflecting surface of mirror 62 and has its upper edge lying just slightly above the level of the mirror apex 110. Mask 66 is positioned between mask 64 and the pack of filters 38, 40 to block transmission of stray light at and below the aligned principal axes 102 and 104 of the lenses. Accordingly, the only light transmitted to lens 32 will lie above the aligned principal axes of the lenses. Mask 64 blocks the entry of emitted light and any stray light into the system's exciting light channel 100.

The rays of the sample's emitted light entering lens 32 will be refracted by lens 32 such that the light rays leaving lens 32 will converge virtually to a point in the optical stop's aperture 94 which directs the sample's emitted light to photomultiplier 28 for measurement.

Photomultiplier 28 measures the intensity of the sample's emitted light. The measured intensity of the emitted light in turn is a measure of the quantity of the fluorescently excited substance which produced the emitted light at the wave length passed by filter 40.

Preferably, lenses 30 and 32 are the same and have equal focal lengths.

In the illustrated embodiment, the object "seen" by lens 30 is the exciting light passing through the optical stop's aperture 84. The exciting light passing through aperture 84 represents the light source as viewed from lens 30.

In accordance with this invention, the length of the path followed by the exciting light from aperture 84 to a desired image point or location in the sample-holding well 20 (as measured along the principal axis from aperture 84 to mirror 60 and from mirror 60 to well 20) is set to equal or at least substantially equal four times the design focal length of lens 30. Lens 30 is positioned at the midpoint of this path. Because of this arrangement, the length of the foregoing path between aperture 84 and lens 30 will be equal to twice the design focal length of lens 30. Likewise, the length of the foregoing path between lens 30 and desired image location in well 20 is also equal to twice the design focal length of lens 30.

This image location in well 20 is selected so that it lies at or at least closely at the surface of the sample in well 20.

Accordingly, where the object (the light source) lies at spot $f_1$ in aperture 84, the sharply focused image will appear at spot $f_2$ centrally in well 20 as shown in FIG. 4.

Because of the optical system thus far described, the image of the exciting light will be sharply focused centrally in well 20 on the sample in well 20 without causing the downwardly reflected exciting light column to strike the side wall of the well or the surface region of plate 18 around the open top of the targeted well. Fluorescent excitation of the sample will therefore be maximized for a given intensity of the exicting light to enhance or strengthen the light emitted by the fluorescently excited sample. In addition, fluorescent excitation of the microtest plate will be reduced by directing the downwardly reflected exciting column into well 20 without striking the well's side wall or the top wall of plate 18.

The length of the path travelled by the exciting light from the optical stop's aperture 84 to the image location in well 20 is selectively adjustable to compensate for imperfections in lens 30. Such imperfections cause small deviates in the lens' focal length from the design or ideal length.

In the illustrated embodiment the foregoing adjustment is accomplished by selectively adjusting the position of optical stop 80 along the principal axis of lens 30. Any suitable means may be employed for adjusting the optical stop 80.

For example, support block 82 may be releasably fixed in place by screws 120 extending through horizontally elongated slots 122 in housing 24 and threaded into tapped bores in block 82 as shown in FIG. 2. If the image of the exciting light is not precisely focused on the desired location in well 20 after system 14 is assembled, screws 120 may be loosened to allow the assembly of block 82 and optical stop 80 to be shifted to a new position along the lens' principal axis where the image of the exciting light focuses more sharply at the desired location in well 20.

The same focusing techniques used for the exciting channel 100 are applied to the emitted light channel 103. In particular, the length of the path followed by the emitted light from the sample in well 20 to a desired image location at the optical stop's aperture 94 (as measured along the principal axis from aperture 94 to mirror 62 and from mirror 62 to well 20) is set to equal or at least substantially equal four times the design focal length of lens 32. Lens 32 is positioned at the midpoint of this path. Because of this arrangement, the length of the path between aperture 94 and lens 32 will be equal to twice the design focal length of lens 32. Likewise, the length of the path between lens 32 and the sample in well 20 is also equal to twice the design focal length of lens 32. Accordingly, where the object (the sample) lies at spot $f_3$ in well 20 the sharply focused image of the sample will appear at spot $f_4$ in the aperture 94, all as shown in FIG. 4.

Because of the foregoing arrangement, substantially the full image of the fluorescently excited sample in well 20 will be sharply focused in aperture 94 and thus on photomultiplier 28 to maximize the intensity of the emitted light detected by the photomultiplier.

Similar to support block 82, support block 90 also is mounted for selective adjustment along the principal axis of lens 32 by screws 124 extending through horizontally elongated slots 126 in housing 24 and threaded into tapped bores in block 90. If the emitted light lens 32 is not precisely focused on the desired location in well 20, screws 124 may be loosened to allow the assembly of block 90, photomultiplier holder 92 and photomultiplier 28 to be shifted as a unit along the principal axis of lens 32 to a new position where the image of the emitted light focuses more sharply on photomultiplier tube 28. In checking for the focus for lens 32, the photomultiplier tube 28 may be replaced by a lamp, thus becoming a light source type of object for lens 32 to provide for the focusing of the lamp's image in well 20.

Although the focus adjustments described for channels 100 and 103 are advantageous for obtaining optimum focusing they are optional in the sense that satisfactory focusing can be achieved in the initial assembly of the component parts of the fluorometer.

In summary, it will be appreciated that the downwardly reflected exciting light beam is directed and confined to strike the sample in well 20 without striking the well's side wall or the top surface of plate 18. It also will be appreciated that photomultiplier 28 detects just those rays of the sample's emitted light passing upwardly through the open top of well 20.

The fluorometer of this invention is therefore particularly suitable for measuring the fluorescence of substances in microtest wells making it unnecessary to transfer samples prepared in microtest plates or strips to special cuvettes or tubes for holding the samples during the fluorometric measurements.

Where the sample-holding microtest plate or strip exhibits a substantial level of fluorescence when exposed to the exciting light in the fluorometer, it will be appreciated that a reference reading may be taken of the plate's native fluorescence to adjust the fluorometric measurements of the samples. Alternatively or additionally, the operator may use non-fluorescent or low-fluorescent microtest plates or strips of the type described in copending application Ser. No. 433,826 filed on even date herewith for Non-Fluorescent Vessels For Holding Test Samples In Fluorescent Assays and assigned to the assignee of the subject application.

In view of the foregoing, it will be appreciated that a reference reading may be taken of the plate's native that the samples may be prepared in microtest plate 18 and that the plate may then be placed in the fluorometer of this invention for individually measuring the fluorescence of the samples in wells 20. Any suitable, conventional mechanism may be utilized for shifting carriage 16 in an X-Y plane to individually and sequentially target the wells 20 for fluorometric measurement to obtain separate fluorometric measurements of the samples in plate 18. Alternatively, it is evident that carriage 16 could be shifted manually to individually target the samples in plate 18.

From the foregoing description it will be appreciated that lens 30 produces a spot image of the exciting light (as seen at perture 84) in well 20 at spot $f_2$. The diameter of aperture 84 is such that the diameter of spot image produced in well 20 is nearly equal to or approaches the diameter of well 20 to excite a maximum area of the sample without causing the downwardly reflected, image-producing exciting light beam to strike the well's side wall of plate's top wall 22 before striking the sample in well 20. For a nonmagnifying lens and a ¼ inch diameter well, the diameter of aperture may be lightly less than ¼ inch.

The diameter of aperture 94 is lightly smaller than the diameter of well 20 or larger if lens 32 is of the type which magnifies the object.

Finally, it will be appreciated that the downwardly reflected, converging beam or column of exciting light enters the open circular top of well 20 at a small acute angle with well's vertically positioned longitudinal axis.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A fluorometer for measuring the fluorescence of a material in an open top microtest well comprising support means for supporting the structure defining said well, a source of exciting light, first means for passing a beam of said exciting light downwardly through the open top of said well to strike and fluorescently excite the material in said well when said well is positioned at a preselected location on said support means, a photodetector, and second means for directing the light which is emitted by the fluorescently excited material and which passes upwardly through the open top of the well to said photodetector for detection thereby, said first means including a lens for focusing said beam on a spot within said well.

2. The fluorometer defined in claim 1 wherein said first means causes said beam of exciting light to converge downwardly through the open top of said well to pass through said spot without first striking the side wall of said well or the surface regions around the top wall of said well.

3. The fluorometer defined in claim 1 wherein said first means causes said beam to follow a preselected light path which extends between said source of exciting light and said spot, said light path having a preselected length equal to a multiple of the focal length of said lens, and said lens being located at the midpoint of said light path.

4. The fluorometer defined in claim 1 wherein said second means includes a further lens, emitted light from the fluorescently excited material in said well being directed along a preselected light path to said photodetector, the length of said light path between a point in said well and said photodetector being equal to a multiple of the focal length of said further lens, and said further lens being located at the midpoint of said light path.

5. The fluorometer defined in claim 1 including means for selectively adjusting the length of the light path followed by the exciting light and the length of the light path followed by the emitted light independently of each other.

6. A fluorometer for measuring the fluoroescence of a material in an open top microtest well comprising support means for supporting the structure defining said well, a source of exciting light, first means for passing a beam of said exciting light downwardly through the open top of the well to strike and fluorescently excite the material in said well without first striking the side wall of said well or the surface regions around the open top of said well when said well is positioned at a preselected location on said support means, a photodetector, and second means for directing light which is emitted by the fluroescently excited material and which passes upwardly through the open top of the well to said photodetector for detection thereby.

7. A fluorometer for measuring the fluorescence of a material in an open top microtest well comprising support means for supporting the structure defining said well, a source of exciting light, first means for passing a beam of said exciting light downwardly through the open top of said well to strike and fluorescently excite the material in said well when said well is positioned at a preselected location on said support means, a photodetector, and second means including a lens for directing the light which is emitted by the fluorescently excited material and which passes upwardly through the open top of the well along a preselected light path to said photodetector for detection thereby, the length of said light path between a point in said well and said photodetector being equal to a multiple of the focal length of said lens, and said lens being located at the midpoint of said light path.

8. A fluorometer for measuring the fluorescence of a material in an open top microtest well comprising support means for supporting the structure defining said well, a source of exciting light, first means for passing a beam of said exciting light downwardly through the open top of said well to strike and fluorescently excite the material in said well when said well is positioned at a preselected location on said support means, a photodetector, and further means for directing the light which is emitted by the fluorescently excited material and which passes upwardly through the open top of said well to said photodetector for detection thereby, said first means including a lens, the length of said light path followed by the exciting light between said source and a point in said well being equal to a multiple of the focal length of said lens, and said lens being located at the midpoint of said light path.

* * * * *

UNITED STATES PATENT AND TRADEMARK OFFICE
CERTIFICATE OF CORRECTION

PATENT NO. : 4,501,970
DATED : February 26, 1985
INVENTOR(S) : Keith E. Nelson

It is certified that error appears in the above-identified patent and that said Letters Patent is hereby corrected as shown below:

Column 2, line 27, change "multitude" to --multiple--.

Column 3, lines 51-57, should read as follows:

--Microtest plate 18 contains a multiplicity of open top wells 20 for receiving and holding test samples in liquid form. Plate 20 may be of the type shown in the previously mentioned Patent No. 4,154,795 or it may be of the type shown in U.S. Patent No. 3,356,462 which issued to N.M. Cooke et al on December 5, 1967. The disclosure of these patents are incorporated into this specification by reference.--

Column 4, line 30, after "in" insert --in turn is mounted on frame 68 by means of a screw and slot--.

Column 4, lines 32 and 33, delete --turn is mounted on frame 68 by means of a screw and slot--.

Signed and Sealed this

Thirtieth Day of July 1985

[SEAL]

Attest:

DONALD J. QUIGG

Attesting Officer     Acting Commissioner of Patents and Trademarks